(12) United States Patent
Fischer et al.

(10) Patent No.: US 6,316,640 B1
(45) Date of Patent: Nov. 13, 2001

(54) PREPARATION OF TETRAHYDROFURAN

(75) Inventors: Rolf Fischer, Heidelberg; Shelue Liang, Ludwigshafen; Rolf Pinkos, Bad Dürkheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/396,356

(22) Filed: Sep. 15, 1999

(30) Foreign Application Priority Data

Sep. 18, 1998 (DE) ............................................. 198 42 847

(51) Int. Cl.$^7$ ................................................. C07D 307/08
(52) U.S. Cl. ............................ 549/429; 549/505; 549/508
(58) Field of Search .................................. 549/429, 475, 549/508, 325, 505

(56) References Cited

U.S. PATENT DOCUMENTS 3,726,905 * 4/1973 Coats et al. ........................ 260/346.1
4,271,080 * 6/1981 Murib .................................. 549/429
5,055,599 * 10/1991 Budge .................................. 549/429

FOREIGN PATENT DOCUMENTS

| 19601375 | 7/1997 | (DE) . |
| 61126080 | * 6/1986 | (JP) . |
| 99/35113 | 7/1999 | (WO) . |
| 99/35136 | 7/1999 | (WO) . |

OTHER PUBLICATIONS

Caplus 106:67144, Tonomura Shoichiro, Cyclic Ethers, Jun. 1986.*

* cited by examiner

Primary Examiner—Alan L. Rotman
Assistant Examiner—Rita Desai
(74) Attorney, Agent, or Firm—Keil & Weinkauf

(57) ABSTRACT

In a process for preparing THF (tetrahydrofuran) by reaction of a 1,4-butanediol-containing reaction mixture over an acid catalyst, the reaction mixture comprises further alcohols different from 1,4-butanediol and is essentially free of water.

7 Claims, No Drawings

PREPARATION OF TETRAHYDROFURAN

The present invention relates to a process for preparing tetrahydrofuran (THF) by reaction of a 1,4-butanediol-containing reaction mixture over an acid catalyst.

Processes for preparing THF from 1,4-butanediol have been known for a long time. K. Weissermel, H.-J. Arpe, Industrielle Organische Chemie, VCH Verlagsgesellschaft, D 69451 Weinheim, 1994, page 111, describes the conversion of 1,4-butanediol into THF by elimination of water with addition of phosphoric acid, sulfuric acid or acid ion exchangers. In this process, the 1,4-butanediol admixed with acid is heated and further 1,4-butanediol is added at the rate at which THF/water distills out.

A disadvantage of this process for preparing THF is that the 1,4-butanediol which is usually used has to be purified before use. The purification is usually carried out by a complicated multistage distillation in which undesired low- and/or high-boiling constituents, including water, are removed. Subsequently, this water-free pure butanediol is converted into THF, with water and undesirable byproducts being formed. For this reason, the THF obtained as product again has to be purified by a multistage distillation after the reaction. Thus, comparable, complicated purification and separation steps have to be carried out twice.

In DE-A-196 01 375, this problem is solved by first removing the volatile organic compounds present in an aqueous butanediol solution by distillation. The aqueous butanediol solution which has been prepurified in this way is dehydrated over an acid aluminum oxide catalyst and the THF-rich fraction obtained is distilled to obtain pure THF. Here, the presence of water in the butanediol solution increases the selectivity of the catalyst. Such aqueous butanediol solutions used as starting material are usually obtained industrially in the preparation of butanediol from acetylene and formaldehyde and subsequent hydrogenation of the butynediol formed. These hydrogenation products comprise water and butanediol together with low boilers such as methanol, propanol and butanol.

It has been proposed already in WO 99/35136 and WO 99/35113, both being non pre-published but having the earlier priority, to produce THF together with γ-butyrolactone and optionally additionally 1,4-butanediol in a multistage process, wherein starting from e.g. dimethyl maleate hydrogenation and cyclization is conducted in two or three partial stages at different catalysts. A typical composition comprises, leaving the said partial stages, 53% γ-butyrolactone, 34% THF, 7% 1,4-butanediol and 3% byproducts (based on an overall conversion rate of 97%. A removal of water, resulting from the synthesis of THF, is only mentioned in relation to the recycling of the gaseous parts. The liquid parts of the reaction effluent are (note FIG. 1 of both WO's), after distillation fraction, THF, methanol, γ-butyrolactone, a recyclable fraction of 1,4-butanediol and the educt dimethyl maleate, heavy boiling organic byproducts and a fraction of water and light boiling organic byproducts. It is expressly mentioned, that the said multistage processes are preferred compared with a process starting with 1,4-butanediol as educt.

There is particular interest in the efficient preparation of THF from essentially nonaqueous butanediol solutions obtained, for example, by hydrogenation of maleic acid or its derivatives, without prior removal of the low boilers such as methanol, propanol, etc. and other by-products present in the hydrogenation product. A problem is that under the reaction conditions of the cyclization of 1,4-butanediol to THF (intramolecular etherification) the other alcohols present in the reaction mixture can also be etherified (intermolecular etherification). Furthermore, the formation of olefins from alcohols, e.g. of butene from butanol, is possible. These by-products would reduce both the yield of THF and the operating lives of the catalyst.

It is an object of the present invention to provide a process for preparing THF from largely water-free 1,4-butanediol in which the butanediol-containing reaction mixture used does not have to be prepurified and the formation of significant amounts of by-products is avoided.

We have found that this object is achieved by using a process for preparing THF by reaction of a 1,4-butanediol-containing reaction mixture over an acid catalyst as the starting point. In the process of the present invention, the reaction mixture comprises further alcohols different from 1,4-butanediol and is essentially free of water.

For the purposes of the present invention, "essentially free of water" means a water content of the reaction mixture of generally less than 5% by weight, preferably less than 2% by weight, particularly preferably less than 1% by weight.

The process of the present invention has the advantage that the 1,4-butanediol-containing reaction mixtures used do not have to be prepurified prior to being converted into THF over an acid catalyst. 1,4-Butanediol is cyclized to THF in the presence of further alcohols without appreciable amounts of by-products being formed. This eliminates the complicated prepurification, thus saving money.

The conversion of 1,4-butanediol-containing reaction mixtures—preferably containing it as the main component, especially containing more than 50% by weight—into THF can be carried out preferably in the liquid phase or also in the gas phase.

The 1,4-butanediol-containing reaction mixtures used as feed in the reaction can be obtained by known methods.

Thus, for example, it is possible to use a 1,4-butanediol-containing reaction mixture which is obtained by the Reppe process from acetylene and formaldehyde and subsequent hydrogenation of the 1,4-butynediol formed, or by acetoxylation or chlorination of butadiene.

Preference is given to using the hydrogenation product from the hydrogenation of a compound selected from the group consisting of maleic acid, maleic monoesters, maleic diesters, maleic anhydride and intermediates formed in the hydrogenation as feed. Examples of such intermediates are succinic anhydride, γ-butyrolactone, succinic acid and succinic diesters. Particular preference is given to using the hydrogenation product of the hydrogenation of maleic diesters as feed in the conversion into THF.

The hydrogenation can be carried out in a known manner in the gas or liquid phase. For example, dimethyl maleate can be hydrogenated in the gas phase over a catalyst, e.g. copper chromite, at superatmospheric pressure and elevated temperature. The hydrogenation product obtained, which is used as feed in the process of the present invention, generally comprises 5–85% by weight of butanediol and 15–95% by weight of alcohol, preferably from 10 to 70% by weight of butanediol and from 15 to 70% by weight of alcohol, particularly preferably from 15 to 60% by weight of butanediol and from 15 to 50% by weight of alcohol. In addition, products such as γ-butyrolactone or succinic diesters can be present in concentrations up to, for example, 30% by weight. The contents of γ-butyrolactone or succinic diesters are generally not critical in the process, but preferably the said contents are not higher than half of the weight content of butanediol. Furthermore, water may be present in a proportion of generally less than 5% by weight, preferably less than 2% by weight, particularly preferably less than 1% by weight, and small amounts of further compounds may also be present. It is possible for THF to be present in the hydrogenation product before it is used in the process of the present invention; the THF content is not critical in the process and can be, for example, from 10 to 30% by weight.

In a preferred embodiment of the invention the feed contains 15 to 60% by weight of butanediol, 15 to 50% by weight of (further) alcohol(s), up to 30% by weight of γ-butyrolactone and/or succinic diester, the content thereof is not higher than half of the weight content of butanediol, and up to 30% by weight of THF, and furthermore, based on the total of all other components being 100% by weight, less than 2% by weight of water.

In place of the entire hydrogenation product, it is also possible to feed only a substream of the hydrogenation product into the reaction to form THF. The reaction product of the reaction to form THF can be fed into the same work-up columns as the substream of the hydrogenation product which has not been reacted further, since both contain similar impurities and by-products. Thus, different apparatuses do not have to be operated for comparable separation tasks.

The alcohols contained in the process of the present invention for preparing THF are generally aliphatic alcohols which are preferably monohydric. Particular preference is given to monohydric aliphatic alcohols having from 1 to 7 carbon atoms and among these methanol, ethanol, iso- and n-propanol and n-butanol are very particularly preferred.

The reaction is generally carried out at from 50 to 300° C., preferably from 65 to 270° C., particularly preferably from 65 to 240° C. It is generally carried out in a pressure range from 0.5 to 80 bar, preferably from 0.8 to 60 bar, particularly preferably from 1 to 40 bar.

Depending on the temperature and pressure conditions selected, the THF and water formed and also the alcohol can go over from the liquid phase to the gaseous phase or remain in the liquid phase. At low reaction pressures, the product stream will leave the reactor as a gas.

In a preferred variant, the reaction to form THF is carried out in the hydrogenation reactor either in the gaseous or preferably in the liquid phase in the presence of hydrogen.

As catalysts, it is in principle possible to use all acidic materials, in homogeneously soluble or heterogeneous form. Examples of homogeneously soluble catalysts are phosphoric acid and sulfuric acid.

Preference is given to using heterogeneous, solid acid catalysts. Examples are the solid oxides of groups 3 to 15 of the Periodic Table of the Elements, where a catalyst may comprise a plurality of elements of the abovementioned groups, acid ion exchangers and heteropolyacids. Preference is given to using solid oxides comprising at least one element of groups 4, 6, 13 and 14 of the Periodic Table of the Elements, particularly preferably $TiO_2$, $ZrO_2$, $CrO_2$, γ-$Al_2O_3$, $SiO_2$ and/or $SnO_2$, with the oxides also being able to be present in combination with one another, as in zeolites. It is also possible to use acid aluminas, sheet silicates and montmorillonites as solid, acid catalysts. Very particular preference is given to catalysts which comprise at least one compound selected from among γ-$Al_2O_3$ and $TiO_2$. To increase their acidity, the catalysts can be pretreated with acids such as phosphoric acid or sulfuric acid.

The reaction can be carried out in the liquid phase over suspended catalysts or in the gas phase over fixed-bed catalysts. For example, the conversion of 1,4-butanediol into THF can be carried out in the gas phase in a fluidized-bed reactor or a tube reactor. The tube reactor can be operated in the downflow or upflow mode. If the reactor is operated in the upflow mode, the high boilers which come from the hydrogenation of maleic acid derivatives or maleic acid and are present in the reaction mixture can accummulate at the bottom of the reactor and be discharged as a bleed stream. This can be discarded or recirculated to earlier process steps, e.g. the hydrogenation.

The feed rate per liter of catalyst is generally from 0.1 to 10 kg/h, preferably from 0.3 to 5 kg/h, particularly preferably from 0.5 to 3 kg/h.

The conversion of the 1,4-butanediol present in the reaction mixture into THF is generally from 99 to 100%. The product from the conversion of 1,4-butanediol into THF (cyclization product) thus has essentially the same composition as the feed except that the 1,4-butanediol present in the feed has been converted into THF and water. The cyclization product generally comprises THF, water of reaction and alcohol. In addition, for example, γ-butyrolactone and succinic esters can be present. They are not affected by the reaction.

The composition of the cyclization product makes it clear that the reaction of 1,4-butanediol-containing reaction mixtures over acid catalysts in the presence of further alcohols to form THF does not result in significant formation of by-products, e.g. of ethers by intermolecular reaction or of olefins.

The cyclization product can be worked up by distillation using methods known to those skilled in the art. EP-B 0 485 484 describes various processes for isolating THF from mixtures comprising THF, one or more low-boiling alcohols and water. Thus, it can be isolated, for example, by extractive distillation with addition of a further component such as 1,4-butanediol, water, ethylene glycol and others. EP-B 0 485 484 also describes a process for isolating THF from the abovementioned mixtures which comprises two successive distillations, the first being carried out at a lower pressure than the second, and a condensation carried out between the distillations. The by-product-enriched mixture obtained from the second distillation is again condensed with the stream from the first distillation and the pure THF obtained in the second distillation is separated off.

A particular advantage is that the alcohol present can be returned to a previous stage, e.g. esterification of maleic anhydride.

In a preferred embodiment, the process of the present invention is carried out in a tube reactor. As acid catalysts, use is made of γ-$Al_2O_3$ and/or $SiO_2$ and/or $TiO_2$, preferably γ-$Al_2O_3$. If the feed stream is not already at the temperature required, the reactor is heated by means of a heating facility, so that the temperature in the catalyst zone is from 50 to 300° C., preferably from 65 to 270° C., particularly preferably from 65 to 240° C. The 1,4-butanediol-containing reaction mixture (feed), preferably the hydrogenation product from the hydrogenation of maleic diesters, is subsequently introduced via the bottom of the reactor. The feed rate per liter of catalyst is generally from 100 to 10,000 ml/h, preferably from 200 to 2400 ml/h, particularly preferably from 500 to 2000 ml/h. After a steady state has been established, the temperature at the front end of the catalyst zone is from 50 to 150° C., preferably from 65 to 100° C., particularly preferably about 70° C., and that in the middle is from 150 to 300° C., preferably from 150 to 250° C., particularly preferably about 200° C. Depending on the temperature and pressure conditions, the product stream vaporizes or is in the form of a liquid. At temperatures of 70° C. at the front end of the catalyst zone and 200° C. in the middle and atmospheric pressure, the product stream vaporizes so that a gaseous reaction product is obtained.

THF is an important solvent for many high polymers and is also employed for the preparation of polytetramethylene glycol which is an intermediate in the production of polyurethanes and Spandex fibers.

The following example illustrates the invention.

EXAMPLE

The percentages reported are percentages by weight determined by gas chromatography (method using internal standard).

Preparation of a 1,4-butanediol-containing Reaction Mixture (Feed)

The feed was obtained by hydrogenation of dimethyl maleate in the gas phase at from 180 to 190° C. and 60 bar over a copper chromite catalyst. It had the following composition (% by weight): 40.1% of methanol, 6.5% of THF, 0.6% of n-butanol, 8.4% of γ-butyrolactone, 37.9% of 1,4-butanediol, 0.1% of methyl 4-hydroxy-butyrate, 2% of dimethyl succinate, 0.7% of 2-(4-hydroxybutoxy) tetrahydrofuran plus water and a number of further compounds whose contents were below 0.1%.

Cyclization to Form THF

A tube reactor was charged with 100 ml (about 63 g) of acid γ-$Al_2O_3$, (4 mm extrudates). It was then heated by means of external heating to bring the temperature in the central catalyst zone to 200° C. The feed (for composition, see above) was then introduced via the bottom of the reactor (50 ml/h). After 30 hours, a steady state had been established. In this steady state, the temperature at the front end of the catalyst zone was about 70° C. and that in the middle was about 200° C. Virtually the entire product stream vaporized at the front end of the catalyst zone so that only about 5% of the catalyst zone were wetted with liquid. The reaction is product comprised 0.1% of dimethyl ether, 39% of methanol, 37.7% of THF, 0.5% of n-butanol, 8.4% of γ-butyrolactone, 0.2% of 1,4-butanediol, 2.2% of dimethyl succinate plus a number of further products whose contents were below 0.1% and water. The individual contents of the products indicated fluctuated slightly from sample to sample, but did not change significantly, even when the feed rate was increased to 80, 120 and 240 ml/h. A total of 8 kg of feed were introduced. At the end of the test run, the catalyst displayed no signs of deactivation. The catalyst extrudates were unaltered.

We claim:

1. A process for preparing THF by reaction of a 1,4-butanediol-containing reaction mixture being a hydrogenation product from the hydrogenation of a maleic diester over an acid catalyst, wherein the reaction mixture comprises 15 to 60% by weight of butanediol, 15 to 50% by weight of (further) monohydric, aliphatic $C_1$- to $C_7$-alcohol(s), up to 30% by weight of γ-butyrolactone and/or succinic diester, the content thereof is not higher than half of the weight content of butanediol, and up to 30% by weight of THF, and furthermore, based on the total of all other components being 100% by weight, less than 2% by weight of water.

2. A process as claimed in claim 1, wherein the monohydric, aliphatic $C_1$-$C_7$-alcohol is an alcohol selected from the group consisting of methanol, ethanol, propanol and n-butanol.

3. A process as claimed in claim 1, wherein the catalysts comprise at least one compound which is selected from the group consisting of $TiO_2$, $ZrO_2$, $CrO_2$, $Al_2O_3$, $SiO_2$ and $SnO_2$.

4. A process as claimed in claim 3, wherein the catalysts comprise at least one compound selected from the group consisting of γ-$Al_2O_3$ and $TiO_2$.

5. A process as claimed in claim 1, wherein the reaction is carried out in the liquid phase over suspended catalysts or in the gas phase over fixed-bed catalysts.

6. A process as claimed in claim 1, wherein the reaction is carried out in the gas phase.

7. A process as claimed in claim 1, wherein the reaction is carried out at from 50 to 300° C. and in a pressure range from 0.5 to 80 bar.

\* \* \* \* \*